| United States Patent [19] | [11] | 4,141,911 |
|---|---|---|
| Matsumoto et al. | [45] | Feb. 27, 1979 |

[54] PRODUCTION OF POLYNUCLEAR DICARBOXYLATOTETRACHROMIUM (III) COMPLEXES

[75] Inventors: Shoichi Matsumoto; Daisuke Nakagawa; Nagao Kaneko, all of Yokohama, Japan

[73] Assignee: Tokyo Shibaura Electric Co., Ltd., Kawasaki, Japan

[21] Appl. No.: 790,901

[22] Filed: Apr. 26, 1977

[30] Foreign Application Priority Data

May 28, 1976 [JP] Japan .................................. 51-62036

[51] Int. Cl.$^2$ .............................................. C07F 11/00
[52] U.S. Cl. ............................................ 260/438.5 R
[58] Field of Search .................. 260/438.5 R, 438.5 C

[56] References Cited

U.S. PATENT DOCUMENTS

| 2,273,040 | 2/1942 | Iler | 260/438.5 X |
|---|---|---|---|
| 2,275,211 | 3/1942 | Urbain et al. | 260/438.5 X |
| 2,544,666 | 3/1951 | Goebel et al. | 260/438.5 X |
| 2,544,667 | 3/1951 | Goebel et al. | 260/438.5 X |
| 2,904,571 | 9/1959 | La Fleur | 260/438.5 C |
| 2,909,545 | 10/1959 | Barnhart | 260/438.5 R |
| 2,951,739 | 9/1960 | Roff | 260/438.5 C X |
| 3,579,555 | 5/1971 | Pangonis | 260/438.5 C |
| 3,705,183 | 12/1972 | Bunger et al. | 260/438.5 C |

Primary Examiner—Helen M. S. Sneed
Attorney, Agent, or Firm—Finnegan, Henderson, Farabow & Garrett

[57] ABSTRACT

Polynuclear dicarboxylatotetrachromium (III) complexes are produced by reacting a dicarboxylic acid with a monobasic chromic (III) salt in a proportion of 4 moles of monobasic chromic (III) salt to 1 mole of dicarboxylic acid. Surface treating agents comprising these complexes provide a surface with desirable properties such as durable water repellency, adhesiveness, antistatic properties, etc.

37 Claims, No Drawings

PRODUCTION OF POLYNUCLEAR DICARBOXYLATOTETRACHROMIUM (III) COMPLEXES

BACKGROUND OF THE INVENTION

I. Field of the Invention

This invention relates to the production of chromium (III) complex compounds and, more particularly, to the production of polynuclear dicarboxylatotetrachromium (III) complexes. It also relates to surface treating agents comprising such chromium complexes and a process for preparing the same.

II. Description of the Prior Art

Heretofore, surface treating agents having a monocarboxylatochromium complex compound as their essential ingredient are known. These surface treating agents can provide the surfaces of paper and other materials with desirable properties such as waterproofness, adhesiveness, etc. However, surface treating agents of this type have the disadvantages that they have poor stability and that the properties provided by them are lacking in durability.

Accordingly, there is a demand for the development of more excellent surface treating atents.

SUMMARY OF THE INVENTION

It is an object of this invention to provide a process for producing dicarboxylatochromium complex compounds that are suitable for use in surface treating agents.

Another object of this invention is to provide a surface treating agent comprising a dicarboxylatochromium complex compound.

Still another object of this invention is to provide a process for preparing a surface treating agent comprising a dicarboxylatochromium complex compound.

In accordance with this invention, there is provided a process for producing polynuclear dicarboxylatotetrachromium (III) complexes having two trivalent chromium atoms coordinated with each carboxylato group, which process comprises reacting a dicarboxylic acid with a monobasic chromic (III) salt in a proportion of 4 moles of monobasic chromic (III) salt to 1 mole of dicarboxylic acid.

DETAILED DESCRIPTION OF THE PREFERRED EMBODIMENTS

Dicarboxylic acids suitable for use in the practice of this invention can be represented by the general formula:

$$HOOC-(R)_n-COOH \quad (I)$$

wherein R is a divalent hydrocarbon-based radical and $n$ is 0 or 1. When $n$ is 0, it is meant that the carbon atoms of the two carboxyl groups are directly bonded with each other (as in the case of oxalic acid). When the R radical exists between the two carboxyl groups, that is, $n$ is 1, R represents a divalent hydrocarbon-based radical. The term "hydrocarbon-based radical" as used in the specification and the appended claims is a generic expression of pure hydrocarbon radicals and hydrocarbon radicals having one or more non-hydrocarbon substituents such as halogen, amino group, hydroxyl group, nitro group, ether group, etc.

Illustrative of the dicarboxylic acids are saturated linear aliphatic dicarboxylic acids (preferably having at least 3 carbon atoms in the R radical) such as oxalic acid, malonic acid, succinic acid, glutaric acid, adipic acid, pimelic acid, suberic acid, azelaic acid, sebacic acid, 1,9-nonanedicarboxylic acid, 1,2-dodecanedioic acid, brassylic acid, thapsic acid, 1,17-heptadecanedioic acid, etc.; unsaturated aliphatic dicarboxylic acids such as maleic acid, fumaric acid, itaconic acid, etc.; alicyclic dicarboxylic acids such as 1-methylcyclopropane-2,3-dicarboxylic acid, truxinic acid, truxillic acid, ciscyclopropane-1,2-diacetic acid, hexahydroterephthalic acid, hexahydrophthalic acid, hexahydroisophthalic acid, 1,2,3,4-tetrahydrophthalic acid, etc.; aromatic dicarboxylic acids such as phthalic acid, isophthalic acid, terephthalic acid, p-phenylenediacetic acid, p-phenylenedipropionic acid, p-phenylenedibutyric acid, p,p'-dicarboxymethylazobenzene, p,p'-biphenyldiacetic acid, p,p'-dicarboxymethyl-transstilbene, etc.; aminodicarboxylic acids such as L-glutamic acid, L-aspartic acid, cystine, etc.; hydroxydicarboxylic acids such as tartaric acid, citric acid, malic acid, tartronic acid, glucosaccharic acid, mucic acid, etc.; dicarboxylic acids having highly polar groups such as chlorosuccinic acid, chloromaleic acid, 2,3-dibromosuccinic acid, perfluorosuccinic acid, perfluoroglutaric acid, perfluoroadipic acid, dichlorophthalic acid, tetrachlorophthalic acid, nitrophthalic acid, etc.; and dicarboxylic acids having ether linkages such as diglycolic acid, etc.

Monobasic chromic (III) salts which are reacted with the above-described dicarboxylic acids to form the chromium complexes of this invention can be represented by the general formula:

$$Cr(OH)X_2 \quad (II)$$

where X is an anion. These salts may be prepared according to any of various procedures, and the present invention will not be limited by the procedure employed for this purpose. A convenient procedure for preparing the basic chromic salts of formula (II) involves reducing chromyl chloride by means of a lower alcohol having up to 7 (preferably up to 5 and more preferably up to 3) carbon atoms such as methyl alcohol, ethyl alcohol, isopropyl alcohol, etc. Chromyl chloride is commercially available, or may be prepared either by reacting chromium trioxide with concentrated hydrochloric acid or by blowing hydrogen chloride gas through a mixture of chromium trioxide and concentrated sulfuric acid.

If isolated chromyl chloride is employed, the reduction of chromyl chloride by a lower alcohol is conveniently carried out in the presence of an inert solvent such as carbon tetrachloride, carbon disulfide, benzene, etc.

The monobasic chromic (III) salts may also be prepared either by reacting a chromic (III) salt hydrate of the general formula:

$$CrX_3 \cdot mH_2O$$

where X is as previously defined and $m$ is a positive number, with an alkali metal or alkaline earth metal hydroxide such as sodium hydroxide, potassium hydroxide, etc. in the presence of a nonaqueous solvent such as methyl alcohol, ethyl alcohol, isopropyl alcohol, etc., or by heating a chromic (III) salt hydrate as described above. Illustrative of the chromic (III) salt hydrate are chromic chloride hexahydrate, chromic bromide hexahydrate, chromic fluoride trihydrate, chromic nitrate nonahydrate, chromic phosphate hemiheptahydrate, various hydrates of chromic sulfate, and the like.

The monobasic chromic (III) salt is an intermediate product. Thus, the salt, instead of being isolated, may be directly reacted with a dicarboxylic acid to produce a dicarboxylatochromium (III) complex within the scope of this invention. For this purpose, a dicarboxylic acid may be previously added to the reaction mixture for the formation of a monobasic chromic (III) salt so that the monobasic chromic (III) salt so formed will immediately react with the dicarboxylic acid. Alternatively, a dicarboxylic acid itself or in solution in a solvent may be added to the reaction mixture containing a monobasic chromic (III) salt which has already been formed.

Generally, the reaction of a monobasic chromic (III) salt with a dicarboxylic acid is carried out by heating under reflux. These two reactants are reacted in a proportion of 4 moles of monobasic chromic (III) salt to 1 mole of dicarboxylic acid. In this manner, dicarboxylatotetrachromium (III) complexes having two trivalent chromium atoms coordinated with each carboxylato group are produced. The products can be represented by the general formula:

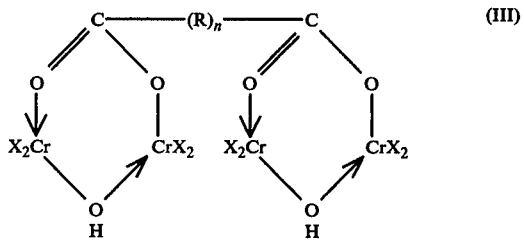

(III)

where R, X and $n$ are as previously defined. These chromium complex are soluble in water and alcohol, and stable even in aqueous solutions.

The chromium complexes produced by the above-described process may be isolated in solid form by suitable means such as filtration followed by removal of the solvent, or the like, and then dissolved in a solvent such as water or alcohol to prepare surface treating agents within the scope of this invention. A more convenient procedure involves reacting a monobasic chromic (III) salt with a dicarboxylic acid in the presence of a lower alcohol, filtering the reaction mixture and concentrating the filtrate containing the chromium complex thus formed, and then diluting the concentrate with a diluent such as water.

Surface treating agents of this invention comprises solutions of the above-described chromium complexes. When such an agent is applied to the surfaces of materials such as paper, fiber, glass, ceramics, etc. and then cured by drying, the chromium complex is firmly bonded with available polar groups of the material surfaces through the chromium atoms to form a film. Thus, they can generally provide the material surfaces with various properties as described below, due to the nature of the R radical present in the chromium complex.

(i) Surface treating agents containing the chromium complexes derived from saturated linear aliphatic dicarboxylic acids or dicarboxylic acid having highly polar groups can provide the surfaces of paper and fiber with water repellency and flexibility. Preferably, these chromium complexes have at least 3 and up to about 15 carbon atoms in the R radical. Preferred complexes are those derived from brassylic acid, 1,17-heptadecanedioic acid and perfluoroadipic acid.

(ii) Surface treating agents containing the chromium complexes derived from saturated linear aliphatic, aromatic, or alicyclic dicarboxylic acids can provide the surfaces of glass, paper, fiber and ceramic substrate with good adhesiveness to various plastics.

(iii) Surface treating agents containing the chromium complexes derived from unsaturated aliphatic dicarboxylic acids, preferably maleic acid, can provide the surfaces of glass, paper, fiber, and ceramic substrates with good adhesiveness to vinyl polymers including polyester.

(iv) Surface treating agents containing the chromium complexes derived from hydroxy- or aminodicarboxylic acids can provide the surfaces of glass, paper, fiber, and ceramic substrates with good adhesiveness to condensation polymers such as phenolic resin. Preferred complexes are those derived from L-aspartic acid and mucic acid.

(v) Surface treating agents containing the chromium complexes derived from substituted dicarboxylic acids having a highly polar group can provide the surfaces of plastics with good antistatic properties. Preferred complexes are those derived from nitrophthalic acid and tetrachlorophthalic acid.

Generally, the dicarboxylatochromium complex comprises from about 0.01 to about 10% by weight of the surface treating agent, the balance being a solvent such as water or alcohols.

The present invention is further illustrated by the following examples.

EXAMPLE 1

Into a 500-milliliter round bottom flask equipped with a stirrer and a dropping funnel, 12.6 grams of sebacic acid, 11.6 grams of absolute ethyl alcohol, and 200 milliliters of carbon tetrachloride were charged and mixed. While this mixture was being stirred, a solution of 38.8 grams of chromyl chloride in 100 milliliters of carbon tetrachloride was slowly added dropwise. After the addition of the chromyl chloride solution was completed, the reaction mixture was gently refluxed for 2 hours. Then, the solvent was removed by evaporation to yield sebacatotetrachromium (III) complex as a dark green solid.

The complex thus produced was subjected to an elemental analysis, obtaining the following result:

|  |  | Result | Calculated |
|---|---|---|---|
| Cr/C | (Weight ratio) | 1.83 | 1.74 |
| Cr/acid | (molar ratio) | 4.2 | 4.0 |

I.R. absorption spectrum of the complex showed that a strong absorption at 1,700 cm$^{-1}$ due to the carbonyl group present in the starting acid disappeared, indicating that the carbonyl group in the acid was coordinated with the chromium atom.

The sebacatotetrachromium complex was dissolved in water to form a surface treating agent containing 1.0% by weight of complex. A craft paper was dipped in the treating agent and was dried at 110° C. for 3 minutes. The water repellency of the thus treated paper was measured according to Japanese Industrial Standard P8137. That is, from a buret one waterdrop was dropped from 1cm height on the treated paper held inclined at an angle of 45°. The waterdrop was wholly slided down the paper, indicating that the treated craft paper exhibited a water repellancy of 10.

EXAMPLE 2

Into a 300-milliliter round bottom flask equipped with a stirrer and a dropping funnel, 100 milliliters of isopropyl alcohol was charged. While the alcohol was being stirred, a solution of 10 grams of chromium trioxide in 22.3 grams of 36% hydrochloric acid was slowly added dropwise under heating. After the addition of the solution of chromium trioxide in hydrochloric acid was completed, the mixture was refluxed for 30 minutes with stirring. Then, the mixture was cooled to 50° C. or below and 6.1 grams of brassylic acid was added. This reaction mixture was refluxed for 30 minutes with stirring. Thereafter, the solvent was removed by evaporation to yield brassylatotetrachromium (III) complex as a dark green solid.

EXAMPLE 3

Into a round bottom flask similar to that employed in Example 1, 20 grams of chromic (III) nitrate nonahydrate and 150 milliliters of ethyl alcohol were charged and brought into solution. While this solution was being stirred, a solution of 2 grams of sodium hydroxide in 50 milliliters of ethyl alcohol was added dropwise. The mixed solution was refluxed for 15 minutes with stirring, and then cooled to room temperature. After addition of 1.5 grams of maleic acid, the reaction mixture was refluxed for 30 minutes with stirring. The by-product, sodium-nitrate, was separated by filtration and then the solvent was removed from the filtrate by evaporation to yield maleatotetrachromium (III) complex as a dark green solid.

The maleatotetrachromium (III) complex produced above was subjected to an elemental analysis, obtaining the following result.

|  |  | Result | Calculated |
|---|---|---|---|
| Cr/C | (Weight ratio) | 4.65 | 4.36 |
| Cr/acid | (molar ratio) | 4.3 | 4.0 |

I.R. absorption spectrum of the complex showed that a strong absorption at 1,700 cm$^{-1}$ due to the carbonyl group present in the starting acid disappeared, indicating that the carbonyl group in the acid was coordinated with the chromium atom.

The maleatotetrachromium complex was dissolved in water to from a surface treating agent containing 2% by weight of complex. A glass cloth was treated with the treating agent and dried. The treated glass cloth was impregnated with an unsaturated polyester to form a prepreg. Likewise, several prepregs were prepared. These prepregs were superposed on one another and pressed under heating to obtain a F.R.P. board 3mm thick.

For comparison, two F.R.P. boards A and B were prepared using a glass cloth treated with an aqueous solution of methacrylatodichromium (III) complex (a complex of chromium with methacrylic acid, a monocarboxylic acid) and non-treated glass cloth, respectively.

The flexural strength of each F.R.P. board was measured according to JIS K6911 both in normal state and after treating in boiling water for 24 hours. The results are shown in Table below.

| | Flexural Strength (Kg/mm$^2$) | |
|---|---|---|
| Sample | Normal State | After boiling treatment |
| This invention | 45 | 35 |
| A | 46 | 24 |
| B | 36 | 18 |

EXAMPLE 4

Chromic (III) chloride hexahydrate, 13.3 grams, was dissolved in 150 milliliters of ethanol. While this solution was being stirred, a solution of 2 grams of sodium hydroxide in 50 milliliters of ethanol was added. The mixed solution was refluxed for 15 minutes with stirring. Then, a solution of 2.6 grams of nitrophthalic acid in 50 milliliters of ethanol was added, and the reaction mixture was refluxed for 30 minutes with stirring. Thereafter, the by-product, sodium chloride, was removed by filtration. Thus, nitrophthalatotetrachromium (III) complex was obtained as an ethanol solution.

The complex solution obtained above was diluted with water to form a surface treating agent containing 5% by weight of complex. The treating agent was coated on the surface of a polystyrene disc having a diameter of 90mm and a thickness of 2mm and was dried. The polystyrene disc thus treated was electrostatically charged to saturation by corona discharge of 5,000 V. The voltage of the polystyrene disc with saturated charge was measured with a rotary sector type electrostatic voltage measuring device and was only 80 V. The voltage value became almost nil within one minute. This shows that the surface treating agent can provide a surface with a superior antistatic property.

The above treated polystyrene did not lose its antistatic property even washed with water or soap water.

Further, the voltage of a polystyrene disc which was not treated with a surface treating agent according to the invention was 2,000 V under the same condition as above, and the voltage value did not decrease even after several minutes.

EXAMPLE 5

To 13.3 grams of chromic (III) chloride hexahydrate dissolved by heating, 3.0 grams of perfluoroglutaric acid was added and the mixture was kept at 180° C. for 15 minutes. After cooling, the mixture was dissolved in hot ethyl alcohol, cooled to 10° C., and then filtered to yield a solution of perfluoroglutaratotetrachromium (III) complex in ethyl alcohol as the filtrate.

EXAMPLE 6

Twenty grams of chromic (III) nitrate nonahydrate was dissolved in 150 milliliters of ethanol. While this solution was being stirred, a solution of 2 grams of sodium hydroxide in 150 milliliters of ethanol was added. The mixed solution was refluxed for 15 minutes with stirring. After a solution of 2.8 grams of p-phenylenedipropionic acid in 50 milliliters of ethanol was added, the reaction mixture was refluxed for 30 minutes with stirring. Then, the reaction mixture was concentrated to a volume of 50 milliliters and filtered to remove sodium sulfate, thereby yielding a solution of p-phenylenedipropionatotetrachromium (III) complex in ethanol as the filtrate.

The results of an elemental analysis of the complex as a solid are as follows.

|  |  | Result | Calculated |
|---|---|---|---|
| Cr/C | (weight ratio) | 1.52 | 1.45 |
| Cr/acid | (molar ratio) | 4.2 | 4.0 |

I.R. absorption spectrum of the complex showed that a strong absorption at 1,700 cm$^{-1}$ due to the carbonyl group present in the starting acid disappeared, indicating that the carbonyl group in the acid was coordinated with the chromium atom.

EXAMPLES 7 to 24

A variety of chromium complexes were produced, following the same procedure as described in Example 6. The starting materials and the products are listed in Table I.

Table I

| | Starting Materials | | | |
|---|---|---|---|---|
| Example | Chromic Salt (0.05 mole) | Dicarboxylic Acid (0.0125 mole) | Solvent | Product |
| 7 | Chromic nitrate nonahydrate | L-Aspartic acid | Ethanol | L-Aspartatotetrachromium (III) complex |
| 8 | " | Tartaric acid | " | Tartaratotetrachromium (III) complex |
| 9 | " | Malonic acid | " | Malonatotetrachromium (III) complex |
| 10 | " | succinic acid | " | Succinatotetrachromium (III) complex |
| 11 | " | Glutaric acid | " | Glutaratotetrachromium (III) complex |
| 12 | " | Adipic acid | " | Adipatotetrachromium (III) complex |
| 13 | " | Pimelic acid | " | Pimelatoterachromium (III) complex |
| 14 | " | Suberic acid | " | Suberatotetrachromium (III) complex |
| 15 | " | Azelaic acid | " | Azelatotetrachromium (III) complex |
| 16 | " | Undecanedioic acic | " | Undecanedioatotetrachromium (III) complex |
| 17 | " | Fumaric acid | " | Fumaratotetrachromium (III) complex |
| 18 | " | P-phenylenediacetic acid | " | P-phenylenediacetatotetrachromium (III) complex |
| 19 | " | Hexahydrophthalic acid | " | Hexahydrophthalatotetrachromium (III) complex |
| 20 | " | L-glutamic acid | " | L-glutamatotetrachromium (III) complex |
| 21 | " | Mucic acid | " | Mucatotetrachromium (III) complex |
| 22 | " | Diglycolic acid | " | Diglycolatotetrachromium (III) complex |
| 23 | " | Perfluoroadipic acid | " | Perfluoroadipatotetrachromium (III) complex |
| 24 | " | 1,17-heptadecanedioic acid | " | 1,17-heptadecanedioatotetrachromium (III) complex |

What we claim is:

1. A process for producing polynuclear dicarboxylatotetrachromium (III) complexes having two trivalent chromium atoms coordinated with each carboxylato group, which consists essentially of reacting a dicarboxylic acid with a monobasic chromic (III) salt in a proportion of 4 moles of basic chromic salt to 1 mole of dicarboxylic acid.

2. A process as claimed in claim 1 wherein said basic chromic salt is monobasic chromic (III) dichloride.

3. A process as claimed in claim 2 comprising reducing chromyl chloride by means of a lower alcohol having up to 7 carbon atoms to form the monobasic chromic (III) dichloride.

4. A process as claimed in claim 2 comprising contacting chromium trioxide with hydrogen chloride to form chromyl chloride and reducing the chromyl chloride by means of a lower alcohol having up to 7 carbon atoms to form the monobasic chromic (III) dichloride.

5. A process as claimed in claim 4 wherein said hydrogen chloride is in the form of an aqueous solution.

6. A process as claimed in claim 1 comprising contacting a chromic (III) salt hydrate with an alkali metal hydroxide to form the monobasic chromic (III) salt.

7. A process as claimed in claim 6 wherein said hydrate is contacted with said hydroxide in a nonaqueous solvent.

8. A process as claimed in claim 1 comprising heating a chromic (III) salt hydrate to form the monobasic chromic (III) salt.

9. A process as claimed in claim 1 wherein the reaction of said dicarboxylic acid with said monobasic chromic (III) salt is carried out in the presence of a solvent.

10. A process as claimed in claim 9 wherein said reaction is carried out under reflux.

11. A process for producing polynuclear dicarboxylatotetrachromium (III) complexes of the general formula

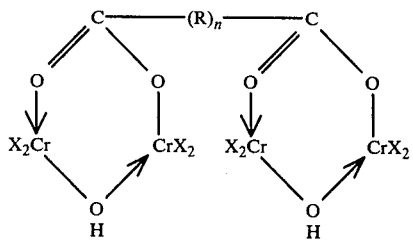

where R is a divalent hydrocarbon-based radical, X is an anion, and $n$ is 0 or 1, which process consists essentially of reacting a dicarboxylic acid of the general formula $HOOC-(R)_n-COOH$ where R and $n$ are as defined above with a monobasic chromic (III) salt of the general formula $Cr(OH)X_2$ where X is as defined above.

12. A process as claimed in claim 11 wherein said dicarboxylic acid is a saturated linear aliphatic acid having up to 15 carbon atoms in the R radical.

13. A process as claimed in claim 11 wherein said dicarboxylic acid is an unsaturated aliphatic acid.

14. A process as claimed in claim 11 wherein said dicarboxylic acid is an aromatic acid.

15. A process as claimed in claim 11 wherein said dicarboxylic acid has an amino or a hydroxyl group in the R radical.

16. A process as claimed in claim 11 wherein said dicarboxylic acid has a highly polar group in the R radical.

17. A process as claimed in claim 11 wherein said dicarboxylic acid is an alicyclic acid.

18. A process as claimed in claim 11 wherein X is halogen or nitrate radical.

19. A surface treating agent comprising a polynuclear dicarboxylatotetrachromium (III) complex having two trivalent chromium atoms coordinated with each carboxylato group.

20. A surface treating agent as claimed in claim 19 wherein said complex is in the form of a solution in a solvent.

21. A surface treating agent as claimed in claim 20 wherein said solvent is water and/or a lower alcohol having up to 7 carbon atoms.

22. A process for preparing a surface treating agent comprising a solution of a polynuclear dicarboxylatotetrachromium (III) complex having two trivalent chromium atoms coordinated with each carboxylato group, which consists essentially of reacting, in the presence of a solvent, a dicarboxylic acid with a monobasic chromic (III) salt in a proportion of 4 moles of monobasic chromic (III) salt to 1 mole of dicarboxylic acid.

23. A process as claimed in claim 22 comprising removing said solvent to yield said complex to solid form and dissolving the solid in a solvent.

24. A process as claimed in claim 22 wherein a lower alcohol having up to 7 carbon atoms is employed as said solvent and which further includes concentrating the resulting solution of said complex and diluting the concentrate with a diluent.

25. A process as claimed in claim 22 wherein said dicarboxylic acid is a saturated linear aliphatic acid having up to about 15 carbon atoms in the R radical.

26. A process as claimed in claim 25 wherein said dicarboxylic acid is 1,17-heptadecanedioic acid or brassylic acid.

27. A process as claimed in claim 22 wherein said dicarboxylic acid is an unsaturated aliphatic acid.

28. A process as claimed in claim 27 wherein said dicarboxylic acid is maleic acid.

29. A process as claimed in claim 22 wherein said dicarboxylic acid is an aromatic acid.

30. A process as claimed in claim 22 wherein said dicarboxylic acid has an amino or a hydroxyl group in the R radical.

31. A process as claimed in claim 30 wherein said dicarboxylic acid is L-aspartic acid or mucic acid.

32. A process as claimed in claim 22 wherein said dicarboxylic acid has a highly polar group in the R radical.

33. A process as claimed in claim 32 wherein said dicarboxylic acid is nitrophthalic acid, perfluoroadipic acid or tetrachlorophthalic acid.

34. A process as claimed in claim 22 wherein said dicarboxylic acid is an alicyclic acid.

35. A process as claimed in claim 34 wherein said dicarboxylic acid is hexahydrophthalic acid.

36. A process as claimed in claim 22 wherein X is halogen or nitrate radical.

37. A process as claimed in claim 29 wherein said dicarboxylic acid is p-phenylenedipropionic acid.

* * * * *